United States Patent
Klein

(10) Patent No.: US 6,703,030 B2
(45) Date of Patent: Mar. 9, 2004

(54) AMINO FRUIT ACID COMPOSITION AND METHOD FOR THE TREATMENT OF SKIN

(76) Inventor: Marvin E. Klein, 27629 Chatsworth St., Farmington Hills, MI (US) 48334

( * ) Notice: Subject to any disclaimer, the term of this patent is extended or adjusted under 35 U.S.C. 154(b) by 0 days.

(21) Appl. No.: 09/772,567

(22) Filed: Jan. 30, 2001

(65) Prior Publication Data

US 2001/0004642 A1 Jun. 21, 2001

Related U.S. Application Data

(63) Continuation-in-part of application No. 09/098,264, filed on Jun. 16, 1998, now Pat. No. 6,197,317.

(51) Int. Cl.⁷ .......................... A61K 6/00; A61K 7/00; A61K 31/195; A01N 37/12; A01N 37/44
(52) U.S. Cl. ..................... 424/401; 514/561; 514/557
(58) Field of Search .................... 424/401; 514/506, 514/561, 557

(56) References Cited

U.S. PATENT DOCUMENTS

| | | | |
|---|---|---|---|
| 3,132,154 A | * 5/1964 | Meyer-Doring | 260/343.7 |
| 3,769,371 A | 10/1973 | Nersasian | 260/900 |
| 4,105,782 A | 8/1978 | Yu et al. | 424/283 |
| 4,105,783 A | 8/1978 | Yu et al. | 424/283 |
| 4,419,343 A | 12/1983 | Pauly | 424/59 |
| 4,707,354 A | 11/1987 | Garlen et al. | 424/47 |
| 4,948,830 A | 8/1990 | Martin et al. | 524/462 |
| 4,983,382 A | 1/1991 | Wilmott et al. | 424/62 |
| 5,091,171 A | 2/1992 | Yu et al. | 424/642 |
| 5,140,043 A | 8/1992 | Darr et al. | 514/474 |
| 5,141,964 A | * 8/1992 | Noel | 252/8.63 |
| 5,248,761 A | * 9/1993 | Hermes | 528/271 |
| 5,478,560 A | 12/1995 | Tominaga et al. | 424/401 |
| 5,679,462 A | 10/1997 | Soga et al. | 428/447 |
| 5,720,949 A | 2/1998 | Davis | 424/78.03 |
| 5,747,635 A | * 5/1998 | Kroner et al. | 528/328 |
| 6,035,780 A | 3/2000 | Badesha et al. | 101/217 |
| 2001/0011272 A1 | 8/2001 | Togawa | |

FOREIGN PATENT DOCUMENTS

| | | |
|---|---|---|
| EP | 0 419 686 A1 | 3/1991 |
| EP | 0 738 757 A2 | 10/1996 |
| WO | WO 91/05009 | 4/1991 |
| WO | WO 96/19182 | 6/1996 |

OTHER PUBLICATIONS

Database JPO on EAST, abstract of JP 361063611 A (Morita et al.), Apr. 1986.*
Database JPO on EAST, abstract of JP 408383138 A (Miyamoto et al.) Oct. 1996.*
Database Derwent on EAST, abstract of DE 1618577 A, Kyowa Hakko Kogyo Co. LTD., Feb. 1972.*

* cited by examiner

*Primary Examiner*—Theodore J. Criares
*Assistant Examiner*—Lauren Q. Wells
(74) *Attorney, Agent, or Firm*—Gifford, Krass, Groh, Sprinkle, Anderson & Citkowski, P.C.

(57) ABSTRACT

A composition for the treatment of skin consists essentially of a carboxylated, acidic amino acid obtained by acidifying an acidic amino acid with a carboxylic acid. The resultant material, which is also referred to as a tricarboxylic acid or an amino fruit acid, has significant benefit for the treatment of a number of skin conditions. In addition, the composition of the present invention is very noncaustic to skin, even when employed at a pH as low as 0.5. Also disclosed herein are therapeutic methods and compositions which employ the carboxylated acidic amino acids.

5 Claims, No Drawings

AMINO FRUIT ACID COMPOSITION AND METHOD FOR THE TREATMENT OF SKIN

RELATED APPLICATIONS

This patent application is a continuation-in-part of patent application Ser. No. 09/098,264 filed Jun. 16, 1998 and entitled "Composition and Method for the Treatment of Skin," now U.S. Patent No. 6,197,317.

FIELD OF THE INVENTION

This invention relates generally to dermatological compositions and methods for their use. More specifically, the invention relates to dermatological compositions based upon acidic amino acids. Most specifically, this invention relates to dermatological compositions based upon carboxylated, acidic amino acids.

BACKGROUND OF THE INVENTION

A large variety of materials and compositions has been employed for the topical treatment of skin conditions caused by drying, photodamage, aging, acne and the like. In addition to being effective and safe, any product used for the treatment of skin conditions should be convenient to formulate, easy to use, have long term stability, and be easy to handle. Additionally, such products should preferably be low in cost.

Retinoic acid, and other retinoid compounds are effective for treating acne, wrinkles and other skin conditions. However, these materials can be very toxic and must be used under close medical supervision, and hence are prescription medications. In addition, retinoids are expensive. Strongly corrosive materials such as phenol, mineral acids and halocarboxylic acids such as trichloroacetic acid have also been used to treat damaged skin. Such corrosive materials achieve a therapeutical effect by causing the outer layers of skin to peel away. These materials must also be used under medical supervision since they can produce serious damage if misapplied.

A number of formulations have been developed for dermatological preparations, using alpha hydroxy acids and alpha keto acids. These acids are used at fairly high concentrations, in clinical settings, to produce superficial peeling of the skin. They are also used at lower concentrations by consumers and paraprofessionals to smooth and condition the skin and reduce wrinkles. In many instances, these materials can still be irritating, and as a result, compositions have been developed wherein buffering agents such as amphoteric compounds or alkaline materials have been added to the acids to raise their pH. Such compositions are shown in U.S. Pat. Nos. 4,105,782; 4,105,783 and 5,091,171. In other instances, skin care compositions have been formulated utilizing ascorbic acid, and such compositions are shown in U.S. Pat. Nos. 4,983,382 and 5,140,043.

In yet other instances, skin care compositions have been prepared utilizing relatively neutral species such as salts. PCT Patent Application WO96/19182 discloses the use of inorganic salts, primarily of magnesium, manganese and various lanthanide elements, for reducing skin irritation. U.S. Pat. No. 5,478,560 discloses the use of salts of mixed amines for treating dry skin.

As can be seen, there is a very large body of prior art directed to topical treatments for various dermatological conditions. The efficacy and safety of the various prior art compositions vary widely as do the cost and ease of formulating and using the compositions. Thus, there is still a need for a composition for treating dermatological conditions, which composition is effective, safe, easy to formulate and use and low in cost.

The parent patent, referred to hereinabove, discloses the fact that certain alpha amino acids (including those referred to as acidic amino acids) are beneficial compounds for the treatment of skin conditions. The parent patent further discloses the use of various acids, including carboxylic acids, to solubilize the amino acid compounds so as to facilitate their incorporation into various dermatological compositions. As will be described in greater detail hereinbelow, it has now been found that when acidic amino acids are solubilized with carboxylic acids, a beneficial interaction occurs which creates a new therapeutic species generally referred to herein as "a carboxylated, acidic amino acid" or a "tricarboxylic acid" or an "amino fruit acid." This new therapeutic material is highly effective for treating a variety of skin conditions. It has a strong antioxidant action; and, it is most surprising that, the material is very non-caustic to skin even at very low pH levels. As will be described hereinbelow, the present invention provides a composition which has very good utility for treating skin conditions associated with dryness, aging, photodamage such as photopigmentation and keratoses as well as acne and seborrheic keratoses. These and other advantages of the present invention will be apparent from the discussion and description which follow.

BRIEF DESCRIPTION OF THE INVENTION

There is disclosed herein a composition for the treatment of skin. The composition is based upon carboxylated, acidic amino acids obtained by treating an acidic amino acid with a carboxylic acid. Some of the preferred acidic amino acids comprise alpha amino dicarboxylic acids, with aspartic and glutamic acid being some particularly preferred acidic amino acids. The carboxylic acids used in this invention can include dicarboxylic acids, hydroxy carboxylic acids, halo-carboxylic acids and the like.

The present invention also concerns a method for formulating the therapeutic compositions; and in accord with the method, an acidic amino acid is reacted with a carboxylic acid to produce the carboxylated, acidic amino acid. The resultant material is disposed in an appropriate carrier, preferably in an amount sufficient to produce a composition with a pH in the range of 0.5 to 5. Also disclosed are therapeutic methods which employ the composition of the present invention.

DETAILED DESCRIPTION OF THE INVENTION

In accord with a first aspect of the present invention, it has been found that certain amino acids have a very beneficial therapeutic effect on the skin. The compositions of the present invention improve the tone and texture of the skin and decrease wrinkling due to drying and aging. The compositions also decrease photodamage to the skin such as photopigmentation and solar keratoses, and the compositions also operate to remove or decrease the severity of acne and seborrheic keratoses. Among the preferred amino acids are the alpha amino acids and within the context of this disclosure it is to be understood that alpha amino acids are those acids in which the amine group is on the carbon which is alpha to the carboxylic acid moiety. In general, alpha amino acids have the formula set forth hereinbelow:

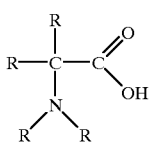

Formula 1 wherein the R groups are independently alkyl, aryl, heterocycles, or hydrogen. It is believed that the alpha configuration results in a beneficial chemical interaction between the amino acid and the skin.

Among some of the most preferred alpha amino acids are the alpha amino dicarboxylic acids. As will be understood by those of skill in the chemical arts, alpha amino dicarboxylic acids are those amino acids having two carboxyl groups, and in which the amine group is alpha to at least one of the carboxyl groups. Two of the particularly preferred alpha amino dicarboxylic acids which may be employed in the practice of the present invention are aspartic acid, shown at Formula 2 hereinbelow, and glutamic acid, shown at Formula 3 hereinbelow.

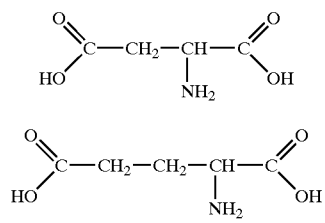

Formula 2

Formula 3

It is to be understood that these amino acids may be also present as salts or ions.

The materials of the present invention are of very low toxicity, and are relatively nonirritating to the skin; hence, they may be used in very high concentrations. However, it has been found that in most instances, amino acid concentrations ranging up to 20%, by weight, are generally effective. In those situations where the composition is being employed in a clinical setting, and particularly when keratoses and other such conditions are being addressed, relatively high concentrations of the composition will be employed. In those instances where the material is being utilized in a nonclinical setting and/or relatively minor conditions are being treated, lower concentrations will suffice. Typically, concentrations of amino acids in the range of 0.5–20% are employed, with concentrations in the range of 2–3% being sufficient for many treatment plans.

The amino acids of the present invention are disposed in a carrier, which in the simplest case comprises water. In other instances, water or alcohol based lotions as well as creams, ointments, gels and other such pharmaceutically acceptable carriers may be utilized. As is known in the art, carriers may further include fragrances, emollients, coloring agents, preservatives, and the like.

In some instances, the alpha amino acids of the present invention are of relatively low solubility in water, weak acids or alcohol. In addressing this problem, it has been found that further enhancements to the compositions of the present invention may be achieved if the alpha amino acid is first dissolved in a solvent system which includes a strong acid therein. As is known in the art, and within the context of this disclosure, strong acids are those acids which are highly ionized in solution and are generally categorized as having a dissociation constant ($K_A$) which is greater than 1. Trichloroacetic acid is one strong acid which is preferably employed in the practice of the present invention. Other strong acids comprise other halocarboxylic acids such as fluoroacetic acids as well as mineral acids such as hydrochloric acid, sulfuric acid, perchloric acid and the like.

In accord with this aspect of the present invention, the alpha amino acid is first dissolved in the solvent system which includes a strong acid therein. For example, it has been found that solutions of up to 20%, by weight, of trichloroacetic acid are highly effective solvents for aspartic acid, which is one of the particularly preferred alpha amino acids of the present invention. After the solution of the alpha amino acid is complete, at least a portion of the remaining strong acid in the solution is neutralized so as to raise the pH of the solution to a therapeutically preferred range. Typically, this range is from approximately 0.5 to approximately 5, and it has been found that the solubilized alpha amino acids remain in solution, in relatively high concentrations, at this pH range. In those instances where the composition of the present invention is being employed in a clinical setting, under professional supervision, relatively low pHs of 0.5 to 2.0 may be effectively employed. In those instances where compositions are being prepared for use in a home, or other nonprofessional setting, relatively higher pHs in the range of 2 to 3 are typically employed. In some instances, effective, stable compositions may be prepared having pHs as high as 5.

Neutralization of the acid may be carried out using any basic material which is compatible with the solvent system and physiologically acceptable. One particularly preferred base comprises urea, and it is believed that the urea, or any resultant salt of urea, further enhances the therapeutic effect of the composition. Other bases which may be advantageously employed are purines, as well as amines. Ammonium hydroxide may also be effectively employed as a base, as may be inorganic bases such as sodium hydroxide and other alkali metal hydroxides.

While not wishing to be bound by conjecture, the inventor speculates that it is possible that the strong acid solubilization and/or neutralization steps may produce new chemical species which further enhance the efficacy of the alpha amino acids of the present invention. Such enhancement may come from the formation of salts or from a chemical rearrangement of the amino acid, as for example by the addition of further carboxyl groups thereto, or by the formation of esters, imines, imides, amides and other such species.

In the broadest sense, the compositions of the present invention are based upon the use of therapeutic compositions of alpha amino acids, and more preferably alpha amino dicarboxylic acids. In yet more specific embodiments of the invention, the compositions are prepared by a method wherein strong acids are first employed to solubilize and/or modify the alpha amino acids, and bases are then employed, as needed, to adjust the pH of the resultant composition.

In accord with still other aspects of the present invention, yet other auxiliary ingredients may be added to the compositions. For example, it has been found that ascorbic acid further enhances the efficacy of the compositions. Most typically, the ascorbic acid, if employed, is present in an amount, by weight, of up to 5% of the composition, although higher concentrations such as 20% may be employed. While there is no lower limit to the amount of ascorbic acid which may be employed, typically, if it is employed at all, it is present in an amount of at least 0.5% by weight. In a most preferred embodiment of the invention, ascorbic acid comprises, by weight, 0.5–5% of the composition. In other instances, citric acid may be included in the compositions, in similar amounts. In yet other instances inorganic salts can be added to the composition, as will be elaborated upon hereinbelow.

Yet other auxiliary ingredients may be employed in the compositions of the present invention. For example, the compositions may be formulated into a cream, gel or lotion base, using any pharmaceutically acceptable carrier. In some instances, the compositions may be formulated into a peel-off mask by employing a film forming carrier such as polyvinyl alcohol or an inorganic, mud pack type carrier such as a clay-based material. As is known in the art, colorings, fragrances, preservatives and the like may be similarly included in the compositions of the present invention.

The following are some examples of compositions in accord with the present invention.

EXAMPLE 1

5 grams of L-aspartic acid was dissolved in the solvent system comprising 100 grams of a 20% aqueous solution of trichloroacetic acid, at room temperature. This produced a clear and complete solution having a pH of less than 1. Solid urea was slowly added to the solution until the pH rose to approximately 3. It was found that this resultant solution was stable and did not crystallize out on standing. The solution was found to have good therapeutic efficacy.

EXAMPLE 2

A second composition was prepared utilizing a portion of the stock material prepared in Example 1. In this example, 3%, by weight, of L-ascorbic acid was dissolved in the stock solution. The thus produced clear solution did not crystallize out on standing, and the pH of the resultant solution was approximately 3.0. The solution was stable on storage and had good therapeutic efficacy.

EXAMPLE 3

A further composition was prepared from the stock solution of Example 1 by dissolving, by weight, 2% citric acid therein. The resultant solution was storage stable, and had a pH of approximately 2.0, and manifested good therapeutic efficacy.

EXAMPLE 4

The stock solution of Example 1 was blended, on a 50% weight basis, with a conventional cold cream base to produce a cream composition. The resultant cream was storage stable and had good therapeutic efficacy.

Yet other compositions can be prepared in accord with the present invention. As discussed above, other alpha amino acids, such as glutamic acid, may be advantageously employed. Still other additives, such as mineral salts, may be employed in the compositions. One particularly preferred group of mineral salts comprises minerals of the type found in the Dead Sea, or synthetic equivalents thereof. These minerals include mixtures of salts of Group I and Group II elements. Most specifically, such Dead Sea minerals comprise mixtures of carbonates, bicarbonates, halides and sulfates of potassium, magnesium, calcium and sodium. Salts, in an amount of up to 5% by weight of the composition, may be advantageously included therein. In some instances, in which a strong acid is used to solubilize the amino acid, the salts themselves may function as bases for the neutralization of excess acid.

Yet other auxiliary materials may be added to the compositions of the present invention. For example, other organic acids, such as lactic acid, salicylic acid and the like may be included in the compositions. Other therapeutic materials such as cortisones or topical anesthetics may be included in the compositions.

The amino acid compositions of the present invention may be disposed in a variety of pharmaceutically acceptable carriers such as lotions, gels and the like as described hereinabove. In accord with yet another aspect of the present invention, it has been found that a carrier base may be advantageously prepared from a mixture of ascorbic acid and mineral salts, most preferably Dead Sea mineral salts as described hereinabove. In addition, the base may include urea. The base solubilizes and stabilizes the compositions of the present invention. While the base may be advantageously employed with the amino acid derived compositions of the present invention, it may also be employed with other dermatological compositions such as compositions based upon hydroxy acids, retinoids, inorganic materials and the like.

The base of the present invention further includes a vehicle, which in the simplest case may comprise water, or the vehicle may comprise lotion, cream, gel or ointment. It has been found that the ascorbic acid and salt interact to produce a smooth, oily composition which readily coats the skin and carries the remaining components of the composition. While not wishing to be bound by speculation, the inventor theorizes that the ascorbic acid and/or the salts interact with one another, and possibly chelate the amino acid or other carboxylic acid to stabilize it and moderate its effects. Urea is one further ingredient which has been found beneficial in the base composition. The urea may be derived from the amino acid derived compositions of the present invention or may be added in addition. The urea functions as a skin moisturizer and softener and facilitates penetration of various components of the composition into the skin.

The ascorbic acid is typically present in the carrier base in an amount of approximately 0.5 to 10%, and the mineral salts are typically present in amounts of between 1 and 20%. In those instances where urea is included in the base composition, it is typically present in an amount of up to 5% and most preferably about 1%.

It is thus to be appreciated that in accord with a first aspect of the present invention, there are provided therapeutic compositions for the treatment of the skin, and methods for their fabrication, wherein the compositions include alpha amino carboxylic acids, and most preferably alpha amino dicarboxylic acids such as aspartic and glutamic acid. The amino acids are preferably solubilized by the action of a strong acid, and the resultant composition neutralized to a therapeutically effective pH with a base such as urea or the like. Yet other ingredients may be further included in the compositions as detailed above. In accord with another aspect of the present invention, there is provided a carrier base which may include ascorbic acid and mineral salts. The base may be used together with the amino acid compositions, or with prior art compositions such as hydroxy acids.

While the foregoing has described the effects of combining strong acids with amino acids, carboxylic acids have been found to have particular benefits in the compositions of the present invention. Therefore, in accord with a second aspect of the present invention, it has been found that carboxylic acids, in particular, can interact with amino acids to produce a novel therapeutic composition having unexpected and beneficial properties for the treatment of skin. Specifically, it has been found that acidic amino acids react, or otherwise interact, with carboxylic acids to produce a species referred to herein as a carboxylated, acidic amino acid. The carboxylated, acidic amino acid has been found to have very good utility for treating skin conditions associated with dryness, aging, photodamage such as photopigmentation and keratoses as well as acne and seborrheic keratoses, among others. The carboxylated, acidic amino acid also has a very good antioxidant effect, and is very compatible with the natural chemistry of the skin.

One very surprising finding is that the carboxylated acidic amino acid material has very low causticity towards skin, even in those instances where it is applied in the form of a composition having a very low pH, such as a pH of 0.5 to 2. This is an unexpected and counterintuitive finding since the prior art has generally recognized that materials for the treatment of skin should have neutral to near neutral pHs if irritation and damage are to be avoided. Thus, the present invention provides a therapeutic material having a high degree of efficacy and a low degree of skin irritation.

The carboxylated, acidic amino acids are formed by the interaction of a carboxylic acid and an acidic amino acid. As used herein, acidic amino acids are generally considered to be those amino acids having an amine group alpha to a carboxyl group. The acidic amino acids include cystine, histidine, arginine, tyrosine, glycine, aspartic acid, glutamic acid, and lysine. In accord with the present invention it has been found that these amino acids can be treated with a carboxylic acid to produce the therapeutic material of the present invention. At present, the precise structure of the carboxylated, acidic amino acid has not been elucidated. While not wishing to be bound by speculation, Applicant presumes that the amino acid and carboxylic acid interact to form a complex, or possibly a new molecular species. In any case, the performance of the new material is significantly different from that of the individual ingredients, particularly with regard to skin irritation. For purposes of discussion, Applicant refers to the carboxylated acidic amino acid material alternatively as being a "tricarboxylic acid" to refer to the fact that one or more carboxyl groups from the carboxylic acid is associated with the amino acid. Applicant also refers to the material as "amino fruit acid." This term was coined to suggest the fact that while the material of the present invention is not a classic fruit acid such as glycolic, lactic or other such fruit acids, it is derived from a fruit acid and an amino acid.

The carboxylated, acidic amino acids of the present invention are believed to have at least three potential hydrogen ion donating carboxyl moieties thereupon. Also, materials of the present invention are modified acidic amino acids and they have been found to have markedly enhanced moisture retention properties when applied to skin, since they, in fact, duplicate the natural moisture retaining amino acid system of the stratum corneum. The materials are very potent antioxidants, and despite the presence of a number of carboxyl groups, are not irritating to the skin; this may be due to the presence of the amino group. It is generally felt that the positively charged hydrogen ions of the carboxyl groups are most responsible for the antioxidant properties since hydrogen ions have the ability to combine with singlet oxygen. In addition, it is speculated that the hydrogen ion plays a significant role in enhancing collagen hydroxyprolination.

While the materials of the present invention may be advantageously prepared from any acidic amino acid and any carboxylic acid, it has been found that aspartic acid and glutamic acids are particularly preferred amino acids. The carboxylic acid may, in some preferred embodiments, comprise one of the alpha hydroxy acids discussed above. Alternatively, it has been found that halocarboxylic acids such as trichloroacetic acid, trifluoroacetic acid and the like may also be employed. Ascorbic acid is another specific carboxylic acid having significant utility in the present invention as are salicylic and lactic acids.

In general, the amino acid and carboxylic acid are combined in an approximately 1 to 1 molar concentration, and the complex forms relatively rapidly at room temperature. The interaction may take place in a solution of an appropriate solvent such as water or alcohol. In some instances, the reaction may take place in an appropriate carrier base such as a gel or cream base. In other instances, the reaction may take place without any additional solvent, most preferably in those instances where the carboxylic acid is a liquid.

In general, the carboxylated, acidic amino acid will be present at a concentration, by weight, of 5 to 30% of a therapeutic formulation. As noted above, the composition is very nonirritating to skin; and hence, relatively concentrated formulations may be employed. In those instances where the compositions are being employed in a clinical setting, still higher concentrations may be employed. Formulations will generally be prepared in accord with the procedures described in the examples hereinabove.

The compositions of the present invention may include various ancillary ingredients as is known in the art. For example, colorings, fragrances, emollients, thickeners and the like may be added to the compositions. In addition, still other therapeutic materials such as antibiotics, disinfectants, analgesics and the like may be incorporated into formulations. Also, compositions may include additional acidic or basic materials for pH adjustment as is known in the art.

While the foregoing has described some specific amino acids and carboxylic acids having utility in the present invention, yet other acids will be readily apparent to one of skill in the art in view of the teaching presented herein. While equimolar mixtures of the carboxylic acid and amino acid are generally employed, an excess of either of the materials may be utilized in certain formulations, for example, for purposes of pH adjustment.

Therefore, it is to be understood that in view of the teaching presented herein, numerous modifications and variations of the present invention may be implemented. The foregoing discussion and description are illustrative of some particular embodiments, but are not meant to be limitations upon the practice thereof. It is the following claims, including all equivalents, which define the scope of the invention.

I claim:

1. A composition for the treatment of skin, said composition consisting essentially of:
    a carboxylated amino acid obtained by acidifying an amino acid selected from the group consisting of: aspartic acid, glutamic acid and combinations thereof, with an alphahydroxy carboxylic acid, said carboxylated amino acid being present in said composition, on a weight basis, in an amount of 0.5–30%; and
    a pharmaceutically acceptable carrier;
    wherein said composition has a pH in the range of 0.5–5.

2. The composition of claim 1, wherein said alphahydroxy acid is glycolic acid.

3. A method for the preparation of a composition for the treatment of skin, said method comprising the steps of:
    providing an amino acid selected from the group consisting essentially of: aspartic acid, glutamic acid, and combinations thereof;

providing an alphahydroxy carboxylated acid;

treating said amino acid with said alphahydroxy carboxylic acid so as to produce a carboxylated amino acid;

providing a pharmaceutically acceptable carrier; and disposing of 0.5–30% by weight of said carboxylated amino acid in said carrier so as to provide a composition having a pH in the range of 0.5–5.

4. A composition for the treatment of skin, said composition consisting essentially of:

a carboxylated amino acid obtained by acidifying an amino acid selected from the group consisting of: aspartic acid, glutamic acid, and combinations thereof with a carboxylic acid, said carboxylated amino acid being present in said composition on a weight basis, in an amount of 0.5–30%; and a pharmaceutically acceptable carrier;

wherein said composition has a pH in the range of 0.5–5.

5. The composition of claim 4, wherein said carboxylic acid glycolic acid.

* * * * *